(12) United States Patent
Rault et al.

(10) Patent No.: US 7,098,220 B2
(45) Date of Patent: Aug. 29, 2006

(54) IMIDAZOPYRIDINE DERIVATIVES, PREPARATION METHOD AND PHARMACEUTICAL COMPOSITIONS CONTAINING SAME

(75) Inventors: Sylvain Rault, Moult (FR); Jean-Charles Lancelot, Le Bourg (FR); Marina Kopp, Caen (FR); Daniel-Henri Caignard, Le-Pecq (FR); Bruno Pfeiffer, Saint Leu la Foret (FR); Jean-Guy Bizot-Espiard, Paris (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/533,699

(22) PCT Filed: Nov. 4, 2003

(86) PCT No.: PCT/FR03/03277

§ 371 (c)(1),
(2), (4) Date: May 3, 2005

(87) PCT Pub. No.: WO2004/043957

PCT Pub. Date: May 27, 2004

(65) Prior Publication Data

US 2006/0069117 A1    Mar. 30, 2006

(30) Foreign Application Priority Data

Nov. 5, 2002  (FR) .................................. 02 13802

(51) Int. Cl.
C07D 471/04 (2006.01)
A61K 31/44 (2006.01)
(52) U.S. Cl. ...................................... 514/303; 546/118
(58) Field of Classification Search ................ 546/118; 514/303
See application file for complete search history.

(56) References Cited

FOREIGN PATENT DOCUMENTS

| EP | 0638568 | 2/1995 |
|---|---|---|
| WO | WO 9825921 | 6/1998 |
| WO | WO 0012089 | 3/2000 |

OTHER PUBLICATIONS

Blache et al, Chemical Abstracts, vol. 131, Abstract No. 58803, 1999.*
Minoru Oguchi, et al., "Molecular Design Synthsesis and Hypoglycemic activity of a series of Thiazolidine-2,4-diones" Journal of Medicinal Chemistry, 2000, Vo. 43(16), p. 3052-3066.

International Search Reprot: PCT FR2003 003277, Mar. 11, 2004.
International Preliminary Examination Report: PCT FR 2003 003277, May 19, 2004.

* cited by examiner

Primary Examiner—Zinna N. Davis
(74) Attorney, Agent, or Firm—Hueschen and Sage

(57) ABSTRACT

Compounds of formula (I):

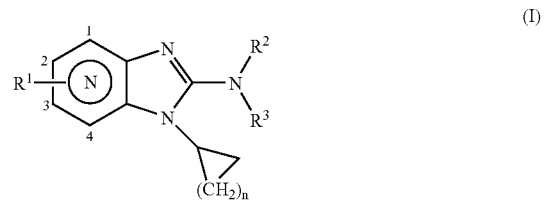

wherein:
  $R^1$ represents hydrogen, halogen, alkyl, polyhaloalkyl, cyano, nitro, hydroxycarbonyl, alkoxycarbonyl, aminocarbonyl, alkylaminocarbonyl or dialkylaminocarbonyl,
  $R^2$ represents hydrogen, alkyl, an optionally substituted aryl, optionally substituted heteroaryl, or $R^{20}$—C(X)— wherein:
    $R^{20}$ represents alkyl, alkoxy, amino, alkylamino, dialkylamino, optionally substituted aryl or optionally substituted heteroaryl,
    X represents oxygen, sulphur, or $NR^{21}$ wherein $R^{21}$ represents hydrogen or alkyl,
  $R^3$ represents hydrogen atom or alkyl,
  n represents integer from 1 to 6 inclusive,
  the representation

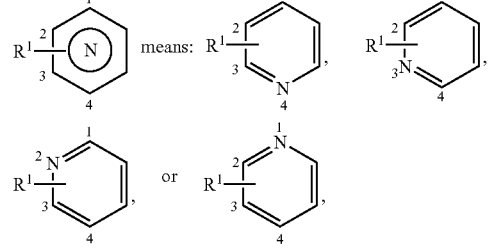

its enantiomers, diastereoisomers and also addition salts thereof with a pharmaceutically acceptable acid or base, and medicinal products containing the same which are useful as AMPK activators.

18 Claims, No Drawings

IMIDAZOPYRIDINE DERIVATIVES, PREPARATION METHOD AND PHARMACEUTICAL COMPOSITIONS CONTAINING SAME

The invention relates to new imidazopyridine compounds, to a process for their preparation and to pharmaceutical compositions containing them.

From the structural point of view, very many examples of imidazopyridine compounds are known in the literature, especially for their therapeutic qualities. By way of example, some compounds are used in the treatment of disorders of the central nervous system (WO 0153263), of viral infections (WO 0100611), of allergies (EP 144101) or of cancers (WO 0244156).

AMP-activated protein kinase (AMPK) is a protein kinase which is involved in the cell response of energy stress. The protein is activated by an increase in the intracellular concentrations of AMP following a fall in the concentration of ATP, during physical exercise, for example.

AMPK phosphorylates and modifies the activity of key enzymes of carbohydrate metabolism. In fact, AMPK plays an important part in lipogenesis, because it inhibits the synthesis of fatty acids and of cholesterol by inactivating acetyl-CoA carboxylase and HMG coreductase. AMPK reduces the expression of fatty acid synthase (FAS), which controls the synthesis of triglycerides.

In addition, AMPK also reduces the expression of one of the key enzymes of neoglucogenesis (PEPCK), which manifests itself in inhibition of the hepatic production of glucose.

Finally, AMPK increases the utilisation of glucose by facilitating the transport of glucose in the muscle.

All those properties combine to make AMPK a target of choice in the treatment of diabetes and of the metabolic disorders associated therewith, the search for pharmacological activators of AMPK accordingly being of fundamental value to the treatment of those pathologies [see Winder W W and Hardie D G: AMP-activated protein kinase, a metabolic master switch: possible roles in type 2 diabetes; Am. J. Physiol., 40: E1–E10, (1999) and cited references].

The Applicant has now found new imidazopyridine compounds having a novel cycloalkyl-imidazopyridine structure, conferring thereon AMPK-activating properties and, more precisely, anti-diabetic and anti-hyperlipidaemic properties.

The present invention relates more especially to compounds of formula (I):

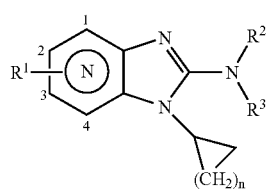

wherein:
$R^1$ represents a hydrogen atom, a halogen atom or an alkyl, polyhaloalkyl, cyano, nitro, hydroxycarbonyl, alkoxycarbonyl, aminocarbonyl, alkylaminocarbonyl or dialkylaminocarbonyl group, $R^2$ represents a hydrogen atom, an alkyl group, an optionally substituted aryl group, an optionally substituted heteroaryl group, or a group $R^{20}$—C(X)— wherein:

$R^{20}$ represents an alkyl group, an alkoxy group, an amino group, an alkylamino group, a dialkylamino group, an optionally substituted aryl group or an optionally substituted heteroaryl group, X represents an oxygen atom, a sulphur atom, or a group $NR^{21}$ wherein $R^{21}$ represents a hydrogen atom or an alkyl group, $R^3$ represents a hydrogen atom or an alkyl group, n represents an integer from 1 to 6 inclusive, the representation

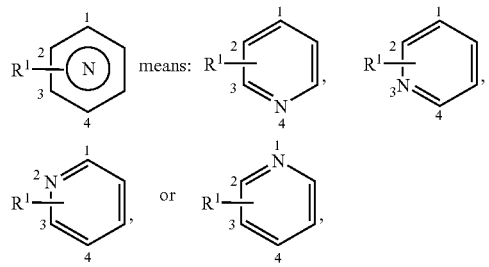

to their enantiomers, diastereoisomers and also to addition salts thereof with a pharmaceutically acceptable acid or base, it being understood that:

the term "alkyl" denotes a linear or branched hydrocarbon chain containing from 1 to 6 carbon atoms, the term "alkoxy" denotes an alkyl-oxy group in which the alkyl chain, which is linear or branched, contains from 1 to 6 carbon atoms, the term "aryl" denotes a phenyl or biphenyl group, the term "polyhaloalkyl" denotes a linear or branched carbon chain containing from 1 to 3 carbon atoms and from 1 to 7 halogen atoms, the term "heteroaryl" denotes a group having from 5 to 11 ring members which is monocyclic or bicyclic, in which at least one of the rings is aromatic, and which contains in the monocyclic ring system or in the bicyclic ring system 1, 2 or 3 hetero atoms selected from nitrogen, oxygen and sulphur, and the term "optionally substituted" associated with the expressions aryl and heteroaryl means that the groups in question are substituted by one or two identical or different substituents selected from halogen atoms and the groups alkyl, alkoxy, polyhaloalkyl, hydroxy, cyano, nitro, amino (optionally substituted by one or two alkyl groups) and —C(O)$R_d$ wherein $R_d$ represents a group selected from hydroxy, alkoxy and amino, it being understood that the heteroaryl group may also be substituted by an oxo group on the non-aromatic moiety of the heteroaryl.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine etc.

The preferred group represented by

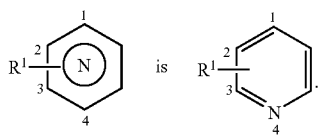

is

An advantageous embodiment of the invention relates to compounds wherein $R^1$ represents a hydrogen atom.

Preferred compounds of the invention are those wherein $R^2$ represents a hydrogen atom or a group $R^{20}$—C(O)—.

Another advantageous embodiment relates to compounds of formula (I) wherein $R^3$ represents a hydrogen atom.

The group $R^{20}$ to which preference is given in accordance with the invention is an alkoxy group and more especially an ethoxy group.

In preferred compounds of the invention, n represents an integer 4, 5 or 6 and more especially 5.

An especially advantageous embodiment of the invention relates to compounds of formula (I) wherein $R^1$ represents a hydrogen atom, $R^2$ represents a hydrogen atom or a group $R^{20}$—C(O)— wherein $R^{20}$ represents an alkoxy group, and n is 4 or 5.

Among the preferred compounds of the invention there may be mentioned more especially 3-cycloheptyl-3H-imidazo[4,5-b]pyridine-2-amine and 3-cyclooctyl-3H-imidazo[4,5-b]-pyridine-2-amine.

The invention relates also to a process for the preparation of compounds of formula (I), characterised in that there is used as starting material the compounds of formula (II):

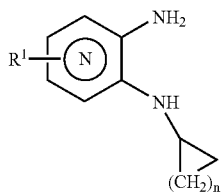

(II)

wherein $R^1$ and n are as defined for formula (I), which compounds of formula (II) are condensed with isothiocyanate compounds (III):

S=C=N—C(X)—$R^{20}$ (III)

wherein X and $R^{20}$ are as defined for formula (I), to yield the intermediates of formula (IV):

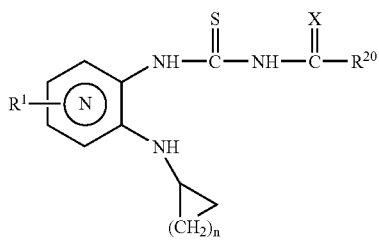

(IV)

wherein $R^1$, n, X and $R^{20}$ are as defined for formula (I), which compounds of formula (IV) undergo intramolecular cyclisation in a basic medium and in the presence of a suitable catalyst to yield the compounds (I/a):

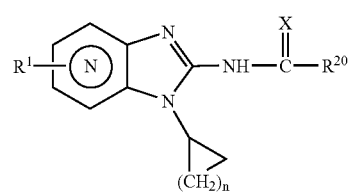

(I/a)

which are particular cases of the compounds of formula (I) wherein $R^1$, n, X and $R^{20}$ are as defined for formula (I), which compounds of formula (I/a) are optionally converted, in an acid medium, into compounds of formula (I/b):

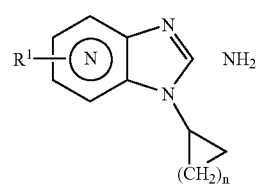

(I/b)

which are particular cases of the compounds of formula (I) wherein $R^1$ and n are as defined for formula (I), in which compounds of formula (I/b) the amine function can be functionalised in a basic medium, with the aid of an alkyl halide Alk-Z (wherein Alk represents an alkyl group and Z represents a halogen atom), to yield the compounds of formula (I/c):

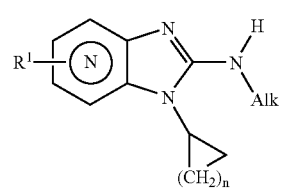

(I/c)

which are a particular case of the compounds of formula (I) wherein $R^1$ and n are as defined for formula (I) and Alk is as defined hereinbefore, which compounds of formulae (I/b) and (I/c) may, in a basic medium, optionally in the presence of suitable catalysts, be reacted with $R^2$-Z' (wherein $R^2$ is as defined for formula (I) and Z' represents a nucleofugal group, such as a halogen atom or a trihaloalkyl group) to yield the compounds of formula (I), which compounds (I/a), (I/b) and (I/c) constitute the totality of the compounds of formula (I) and:
  which may, where necessary, be purified according to a conventional purification technique,
  which are separated, where necessary, into the stereoisomers according to a conventional separation technique,
  which are converted, if desired, into their addition salts with a pharmaceutically acceptable acid or base, it being understood that:

at any time considered to be appropriate in the course of the process described above, for the requirements of synthesis the carbonyl, amino or alkylamino group(s) of the starting reagents (II) and (III) may be protected and then, after condensation, deprotected, the reagents (II) and (III) are prepared according to known procedures described in the literature.

The compounds exhibit especially an excellent activity in reducing triglyceride and blood glucose levels. Those properties justify their use therapeutically in the treatment and/or prophylaxis of hyperglycaemia, dyslipidaemia and, more especially, in the treatment of non-insulin-dependent, type II diabetes, of obesity, of glucose intolerance and of complications of diabetes especially in the cardiovascular area.

The activity of those compounds is also recommended for the treatment and/or prophylaxis of other diseases including type I diabetes, hypertriglyceridaemias, metabolic syndrome, insulin resistance, dyslipidaemia in diabetics, hyperlipidaemia and hypercholesterolaemia.

The present invention relates also to pharmaceutical compositions comprising as active ingredient at least one compound of formula (I), alone or in combination with one or more inert, non-toxic, pharmaceutically acceptable excipients or carriers.

Among the pharmaceutical compositions according to the invention there may be mentioned more especially those that are suitable for oral, parenteral and nasal administration, tablets or dragées, sublingual tablets, gelatin capsules, lozenges, suppositories, creams, ointments, dermal gels etc.

The useful dose varies according to the age and weight of the patient, the nature and severity of the disorder and the administration route, which may be oral, nasal, rectal or parenteral. Generally, the unit dose ranges from 0.1 to 500 mg per 24 hours, for treatment in from 1 to 3 administrations.

The Examples that follow illustrate the invention, without limiting it in any way. The structures of the compounds described have been confirmed by customary spectroscopic and spectrometric techniques.

The starting materials used are known products or are prepared according to known procedures.

Preparation 1: $N^2$-Cyclohexyl-2,3-pyridinediamine

Step a: N-Cyclohexyl-3-nitro-2-pyridineamine

A mixture composed of 0.1 mol (15.85 g) of 2-chloro-3-nitropyridine and 0.1 mol (11.50 ml) of cyclohexylamine is heated at 120° C. for 4 hours in 250 ml of DMF in the presence of potassium carbonate (13.81 g). The solution is then extracted with 200 ml of ether and the organic phase is washed three times with water. After drying over magnesium sulphate, the ether is evaporated off.

Step b: $N^2$-Cyclohexyl-2,3-pyridinediamine 800 ml of ethanol, 0.05 mol (11.06 g) of the nitrated compound prepared in the preceding Step and 3.5 g of palladium-on-carbon are introduced into an autoclave. The mixture is heated at 60° C. for 30 minutes under 50 kg of hydrogen and then stirred horizontally at ambient temperature for 3 hours in order to homogenise the solution. After that time, the solution is filtered through a Büchner and then a double filter in order to remove the final residues of palladium-on-carbon, and the ethanol is evaporated off under reduced pressure.

Preparation 2: $N^2$-Cycloheptyl-2,3-pyridinediamine

The experimental protocol is identical with that used in Preparation 1, starting from cycloheptylamine instead of cyclohexylamine in Step a.

Preparation 3: $N^2$-Cyclooctyl-2,3-pyridinediamine

The experimental protocol is identical with that used in Preparation 1, starting from cyclo-octylamine instead of cyclohexylamine in Step a.

EXAMPLE 1

Ethyl 3-cyclohexyl-3H-imidazo[4,5-b]pyrid-2-ylcarbamate

Step a: Ethyl {[2-(cyclohexylamino)-3-pyridyl]imino}(diethylamino)methylcarbamate A mixture of 0.02 mol (3.82 g) of 3-amino-2-cyclohexylaminopyridine from Preparation 1 and 0.02 mol of ethoxycarbonyl isothiocyanate is stirred in 50 ml of DMF at ambient temperature for 3 hours. The solution is then cooled to 0° C., and 0.05 mol of dipropylamine and then 0.02 mol of mercuric chloride are added in succession. After 15 minutes, the ice bath is removed and the solution is stirred at ambient temperature for 4 hours. After diluting the solution with 100 ml of ethyl acetate, filtration is carried out over Celite and the solvents are evaporated off under reduced pressure. The resulting crude product is then recrystallised from acetonitrile.

Step b: Ethyl 3-cyclohexyl-3H-imidazo[4,5-b]pyrid-2-ylcarbamate 0.0048 mol of the compound prepared in the preceding Step is dissolved in 100 ml of a solution of methanol and 15% sodium hydroxide solution (50/50). After heating the solution at reflux for 3 hours, the methanol is evaporated off. The precipitate so obtained is suction filtered, washed with water and recrystallised from acetonitrile.

Melting point: 264° C.

EXAMPLE 2

Ethyl 3-cycloheptyl-3H-imidazo[4,5-b]pyrid-2-ylcarbamate

The experimental protocol is identical with that used in Example 1, starting in Step a from 3-amino-2-cycloheptylaminopyridine from Preparation 2 instead of 3-amino-2-cyclohexylaminopyridine.

Melting point: 177° C.

EXAMPLE 3

3-Cyclohexyl-3H-imidazo[4,5-b]pyridine-2-amine

The compound of Example 1 is added to 100 ml of a dioxane solution saturated with gaseous HCl, and the solution is heated at reflux for 12 hours. After cooling the solution, the precipitate is suction filtered, washed with sodium bicarbonate and then recrystallised from acetonitrile.

Melting point: 210° C.

EXAMPLE 4

3-Cycloheptyl-3H-imidazo[4,5-b]pyridine-2-amine

The experimental protocol is identical with that used in Example 3, using the compound of Example 2 as starting material.

Melting point: 210° C.

EXAMPLE 5

3-Cyclooctyl-3H-imidazo[4,5-b]pyridine-2-amine

The experimental protocol is identical with that used in Example 1, starting in Step a from 3-amino-2-cyclooctylaminopyridine of Preparation 3 instead of 3-amino-2-cyclohexylaminopyridine.

Melting point: 198° C.

Pharmacological Study

Example A

AMPK Activity in a Cell Model: Hepatocytes Isolated from Rats

The hepatocytes are isolated according to the technique of Berry and Friend [J. Cell Biol, 43, 506–520 (1969)]. The AMPK activity was measured according to the method described by Davies el al. [Eur. J. Biochem., 186, 123–128 (1989)]. The latter involves phosphorylation starting from [γ-$^{32}$P]-ATP of a peptide substrate (SAMS), based on the sequence surrounding the site phosphorylated by the AMPK of the ACC. The reaction for measuring the AMPK activity ends with the deposition of an aliquot of the reaction medium on a phosphocellulose paper (Whatman P81), on which the SAMS peptide is fixed and the radioactivity of which is measured after washing.

By way of example, the compound of Example 4 activates AMPK, after 30 minutes at a concentration of 500 μM, by 312% (compared with the base value), whereas the same concentration of AICA riboside, used as reference, under the same conditions, activates it by 178%.

Example B

Hypolipaemic Activity

The products of the invention were tested in vivo in the obese ob/ob mouse, used as a model of obesity-associated insulin resistance. By way of example, the compound of Example 4 significantly reduces the triglycerides at 125 mg/kg per os whereas, with metformin, the same reduction is obtained at 250 mg/kg per os.

In this model, the compounds of the invention have thus been shown to be powerful hypolipaemic agents.

Example C

Pharmaceutical Composition

Formulation for the preparation of 1000 tablets each containing 5 mg:

| | |
|---|---|
| Compound of Example 4 | 5 g |
| Hydroxypropylmethylcellulose | 2 g |
| Wheat starch | 10 g |
| Lactose | 100 g |
| Magnesium stearate | 3 g |

The invention claimed is:

1. A compound of formula (I):

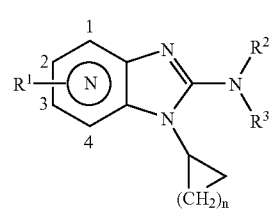

wherein:
R$^1$ represents hydrogen, halogen, alkyl, polyhaloalkyl, cyano, nitro, hydroxycarbonyl, alkoxycarbonyl, aminocarbonyl, alkylaminocarbonyl or dialkylaminocarbonyl,
R$^2$ represents hydrogen, alkyl, optionally substituted aryl, optionally substituted heteroaryl, or R$^{20}$—C(X)— wherein:
  R$^{20}$ represents alkyl, alkoxy, amino, alkylamino, dialkylamino, optionally substituted aryl or optionally substituted heteroaryl,
  X represents oxygen, sulphur, or NR$^{21}$ wherein R$^{21}$ represents hydrogen or alkyl,
R$^3$ represents hydrogen or alkyl,
n represents an integer from 1 to 6 inclusive,
the representation

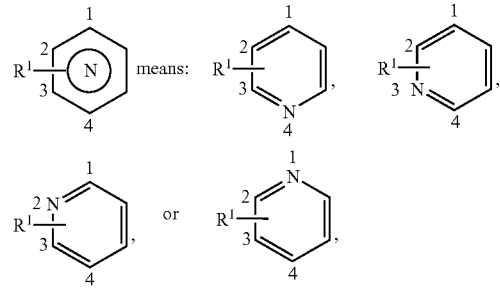

its enantiomers, diastereoisomers and addition salts thereof with a pharmaceutically acceptable acid or base,
  the term "alkyl" denotes linear or branched hydrocarbon chain having from 1 to 6 carbon atoms,
  the term "alkoxy" denotes an alkyl-oxy in which the alkyl chain, which is linear or branched, has from 1 to 6 carbon atoms,
  the term "aryl" denotes phenyl or biphenyl,
  the term "polyhaloalkyl" denotes a linear or branched carbon chain having from 1 to 3 carbon atoms and from 1 to 7 halogen atoms,
  the term "heteroaryl" denotes a group having from 5 to 11 ring members which is monocyclic or bicyclic, in which at least one of the rings is aromatic, and which contains in the monocyclic ring system or in the bicyclic ring system 1, 2 or 3 hetero atoms selected from nitrogen, oxygen and sulphur, and
  the expression "optionally substituted" associated with the expressions aryl and heteroaryl means that the groups in question may be substituted by one or two identical or different substituents selected from halogen, alkyl, alkoxy, polyhaloalkyl, hydroxy, cyano, nitro, amino (optionally substituted by one or two alkyl groups) and —C(O)R$_d$ wherein R$_d$ represents a group selected from hydroxy, alkoxy and amino, and wherein the heteroaryl may also be substituted by an oxo moiety on the non-aromatic moiety of the heteroaryl.

2. A compound of claim 1, wherein the representation

3. A compound of claim 1, wherein R$^1$ represents hydrogen.

4. A compound of claim 1, wherein R$^2$ represents hydrogen.

5. A compound of claim 1, wherein R$^2$ represents a group R$^{20}$—C(O)—.

6. A compound of claim 1, wherein R$^3$ represents hydrogen.

7. A compound of claim 1, wherein R$^{20}$ represents alkoxy.

8. A compound of claim 1, wherein n represents an integer from 4 to 6 inclusive.

9. A compound of claim 1, wherein

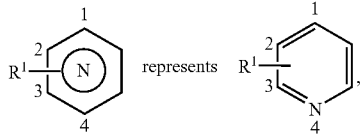

R$^1$ represents hydrogen, R$^2$ represents hydrogen or a group R$^{20}$—C(O)—, wherein R$^{20}$ represents alkoxy, and n is 4 or 5.

10. A compound of claim 1, which is 3-cycloheptyl-3H-imidazo[4,5]pyridine-2-amine.

11. A compound of claim 1, which is 3-cyclooctyl-3H-imidazo[4,5]pyridine-2-amine.

12. A pharmaceutical composition useful as an AMPK activator, comprising as active principle and effective amount of a compound as claimed in claim 1, together with one or more inert, non-toxic, pharmaceutically acceptable excipients or vehicles.

13. A method for treating a living animal body afflicted with a condition selected from non-insulin-dependent, type II diabetes, obesity, type I diabetes, hyperlipidaemia, hypercholesterolaemia and their cardiovascular complications, comprising the step of administering to the living animal body an amount of a compound of claim 1, which is effective for alleviation of the condition.

14. A method for treating a living animal body afflicted with a condition selected from type I and II diabetes and their cardiovascular complications, comprising the step of administering to the living animal body an amount of a compound of claim 1, which is effective for alleviation of the condition.

15. A method for treating a living animal body afflicted with a condition selected from type I and II diabetes, comprising the step of administering to the living animal body an amount of a compound of claim 1, which is effective for alleviation of the condition.

16. A method for treating a human afflicted with a condition selected from non-insulin-dependent, type II diabetes, obesity, type I diabetes, hyperlipidaemia, hypercholesterolaemia and their cardiovascular complications, comprising the step of administering to the human an amount of a compound of claim 1, which is effective for alleviation of the condition.

17. A method for treating a human afflicted with a condition selected from type I and II diabetes and their cardiovascular complications, comprising the step of administering to the human an amount of a compound of claim 1, which is effective for alleviation of the condition.

18. A method for treating a human afflicted with a condition selected from type I and II diabetes, comprising the step of administering to the human an amount of a compound of claim 1, which is effective for alleviation of the condition.

* * * * *

UNITED STATES PATENT AND TRADEMARK OFFICE
CERTIFICATE OF CORRECTION

PATENT NO. : 7,098,220 B2
APPLICATION NO. : 10/533699
DATED : August 29, 2006
INVENTOR(S) : Sylvain Rault et al.

It is certified that error appears in the above-identified patent and that said Letters Patent is hereby corrected as shown below:

Column 9, Line 41:   "[4,5]" should be -- [4,5-b] --.

Column 9, Line 43:   "[4,5]" should be -- [4,5-b] --.

Signed and Sealed this

Twenty-first Day of November, 2006

JON W. DUDAS
*Director of the United States Patent and Trademark Office*